(12) United States Patent
Gross et al.

(10) Patent No.: US 11,759,279 B2
(45) Date of Patent: Sep. 19, 2023

(54) PACKAGING FOR A MEDICAL DEVICE

(71) Applicant: BioGenware, LLC, Columbia, SC (US)

(72) Inventors: Jeffrey G Gross, Columbia, SC (US); John Lowsky, Jr., Columbia, SC (US)

(73) Assignee: BioGenware, LLC, Columbia, SC (US)

( * ) Notice: Subject to any disclaimer, the term of this patent is extended or adjusted under 35 U.S.C. 154(b) by 0 days.

(21) Appl. No.: 17/317,961

(22) Filed: May 12, 2021

(65) Prior Publication Data

US 2021/0369380 A1 Dec. 2, 2021

Related U.S. Application Data

(60) Provisional application No. 63/119,212, filed on Nov. 30, 2020, provisional application No. 63/030,995, filed on May 28, 2020.

(51) Int. Cl.
*A61B 50/30* (2016.01)
*A61B 50/00* (2016.01)
*A61B 17/02* (2006.01)

(52) U.S. Cl.
CPC .......... *A61B 50/30* (2016.02); *A61B 17/0231* (2013.01); *A61B 2050/0076* (2016.02); *A61B 2050/0084* (2016.02)

(58) Field of Classification Search
CPC . A61B 50/33; A61B 50/30; A61B 2050/0076; A61B 2050/0084; A61B 17/0231; B65D 25/10; B65D 25/101; B65D 1/24; B65D 81/113
USPC ........................................ 206/438, 363, 523
See application file for complete search history.

(56) References Cited

U.S. PATENT DOCUMENTS

| | | | |
|---|---|---|---|
| 3,409,349 A | 11/1968 | Boyle et al. | |
| 5,171,254 A | 12/1992 | Sher | |
| 5,374,272 A | 12/1994 | Arpa et al. | |
| 5,433,190 A | 7/1995 | Sunalp | |
| 5,938,674 A | 8/1999 | Terry | |
| 6,012,577 A * | 1/2000 | Lewis | A61L 2/26 206/439 |
| 6,022,365 A | 2/2000 | Aufaure et al. | |
| 6,083,155 A | 7/2000 | Trese | |
| 6,267,752 B1 | 7/2001 | Svetliza | |
| 6,440,065 B1 | 8/2002 | Hered | |
| D489,130 S | 4/2004 | Sinding | |
| D498,531 S | 11/2004 | Sinding | |
| 8,066,635 B2 | 11/2011 | Beck | |
| 8,584,849 B2 * | 11/2013 | McCaffrey | A61M 25/002 206/364 |
| 8,685,068 B2 * | 4/2014 | Sixto | A61B 50/30 606/915 |

(Continued)

FOREIGN PATENT DOCUMENTS

| | | |
|---|---|---|
| CN | 101167672 A | 4/2008 |
| CN | 101695460 A | 4/2010 |

(Continued)

*Primary Examiner* — Steven A. Reynolds
(74) *Attorney, Agent, or Firm* — Dority & Manning, P.A.

(57) ABSTRACT

Packaging for a medical device, such as but not limited to an eyelid speculum, is provided. The packaging enables for the shipment, storage, sterilization of the medical device in a secure and efficient manner while also maintaining the sterility of the device post-sterilization and allowing for the easy removal of the medical device from the packaging without compromising the device's sterility.

21 Claims, 7 Drawing Sheets

(56) References Cited

U.S. PATENT DOCUMENTS

| | | | |
|---|---|---|---|
| 8,833,560 B2* | 9/2014 | Shih | B65D 81/058 |
| | | | 206/592 |
| 8,936,550 B2 | 1/2015 | Urano et al. | |
| 9,668,916 B2 | 6/2017 | Thompson | |
| 10,130,351 B2 | 11/2018 | Shugarman | |
| 11,051,807 B2* | 7/2021 | Shelton, IV | A61B 50/20 |
| 2007/0270657 A1 | 11/2007 | Stephenson et al. | |
| 2009/0227846 A1 | 9/2009 | Beck | |
| 2012/0071726 A1 | 3/2012 | Beck | |
| 2013/0277261 A1* | 10/2013 | Kinyon | A61F 2/0095 |
| | | | 206/438 |
| 2015/0021221 A1* | 1/2015 | Hendrickson | A61B 50/20 |
| | | | 206/438 |
| 2016/0030239 A1 | 2/2016 | Akura et al. | |
| 2019/0167375 A1* | 6/2019 | Niese | A61B 50/33 |

FOREIGN PATENT DOCUMENTS

| | | |
|---|---|---|
| CN | 206597081 U | 10/2017 |
| CN | 108143540 A | 6/2018 |
| CN | 209199692 | 1/2019 |
| DE | 9320127 U1 | 4/1994 |
| FR | 2827497 A1 | 1/2003 |
| GB | 114051 A | 3/1918 |
| GB | 2 382 779 B | 6/2006 |
| GB | 2507285 B | 11/2016 |
| KR | 101198016 B1 | 11/2012 |
| TW | 200735852 A | 10/2007 |
| WO | WO 2011/077115 A1 | 6/2011 |
| WO | WO 2017/027763 A1 | 2/2017 |
| WO | WO 2018198686 A1 | 11/2018 |

\* cited by examiner

PACKAGING FOR A MEDICAL DEVICE

CROSS-REFERENCE TO RELATED APPLICATIONS

The present application claims priority to U.S. Patent Application Ser. No. 63/030,995, filed on May 28, 2020 and U.S. Patent Application Ser. No. 63/119,212, filed on Nov. 30, 2020, the entire contents of which are incorporated herein by reference.

BACKGROUND OF THE INVENTION

The traditional eyelid speculum is one of the most commonly used devices in ophthalmology. For example, recent surveys indicate that physicians in the United States use a traditional eyelid speculum at least 75% of the time when performing intravitreal injections, and the number of intravitreal injections performed yearly to treat conditions such as macular degeneration, diabetic retinopathy, and retinal vein occlusions, among other conditions, is estimated to be approximately 6 million in the United States and 22 million worldwide. One particular example of a traditional eyelid speculum is known by those in the art as the Barraquer speculum. The Barraquer speculum includes open or solid wire loops that are designed to retract the eyelids during ophthalmic surgery or minor office procedures, such as during eye injections. The purpose of an eyelid speculum is to retract the eyelids of a patient to allow for consistent exposure for surgical maneuvers, intravitreal injections, imaging procedures, and the like. The Barraquer speculum is typically formed of metal and wire and is a large device that is often intimidating to patients, with many patients finding the insertion of the Barraquer speculum to be more uncomfortable than the surgery or office procedure that follows. Moreover, the Barraquer speculum is not disposable and must be autoclaved for sterile reuse, where there is a risk that the Barraquer speculum may not be sterile if the autoclave procedure is not conducted properly. Another instrument that may be used is the Desmarres or Jaffe eyelid retractor, but, like the Barraquer speculum, it is often formed from metal, is not disposable, and must be autoclaved before reuse. Therefore, it shares many of the disadvantages of the Barraquer speculum.

As an alternative, some physicians opt to manually retract a patient's eyelids without the use of a speculum. Although many patients indicated this is more comfortable than eyelid retraction via a Barraquer speculum, manual retraction may not provide the safety to adequately expose an injection site and may not prevent contact of an instrument (e.g., a needle) with a patient's eyelashes, which puts the patient at risk for developing an infection. Further, involuntary eyelid closure during injections has been shown to lead to increased levels of needle contamination when no eyelid speculum is used.

As less bulky, easy-to-use, and/or smaller eyelid speculums and other medical devices are developed to overcome the problems addressed above, one concern is the packaging and sterilization of the eyelid speculums and other medical devices. For instance, the smaller and less bulky a medical device is, the more difficult it is to ship without damaging it. Further, the smaller and less bulky a medical device is, the more difficult it is to maintain sterility once it is removed from a sterilization pouch. As such, there is a need for packaging for such devices that can allow for the storage, shipment, sterilization, and removal of such medical devices in a safe, efficient, and sterile manner.

SUMMARY OF THE INVENTION

In accordance with one exemplary embodiment of the present invention a medical device packaging is provided.

According to one particular embodiment of the present invention, a medical device packaging housing a medical device is provided. The medical device packaging includes a front wall, a back wall, a bottom wall, a first side wall, and a second side wall, wherein the front wall includes a front lip positioned between a first portion and a second portion of the front wall; wherein the front lip has a height that is greater than a height of the first portion and the second portion of the front wall; wherein a first protrusion extends from an inner surface of the front wall, wherein the front wall and the back wall extend upward from the bottom wall in a y-direction, wherein the bottom wall extends between the first side wall and the second side wall in the x-direction, and wherein the first side wall and the second side wall extend between the front wall and the back wall in the z-direction.

In one embodiment, an opening can be present on the bottom wall adjacent the front wall and a second protrusion can extend from an inner surface of the bottom wall.

In another embodiment, the medical device housed by the medical device packaging can be an eyelid speculum. Further, the eyelid speculum housed by the medical packaging can include a central ring having an upper surface, a lower surface, an inner side surface, an outer side surface, a first end, and a second end. The first end and the second end can be separated by a gap, and the central ring can define an opening. The eyelid speculum can also include a first eyelid margin holder extending outwardly from the outer surface of the central ring at the first end and having an upper portion and a lower portion, a second eyelid margin holder extending outwardly from the outer surface of the central ring at the second end and having an upper portion and a lower portion, a first finger tab extending upwardly from the upper portion of the first eyelid margin holder, and a second finger tab extending upwardly from the upper portion of the second eyelid margin holder.

In an additional embodiment, the eyelid speculum can be pressed into the medical device packaging with the outer surface of the eyelid speculum facing the front wall of the medical device packaging.

In one more embodiment, the eyelid speculum can be pressed into the medical device packaging until it locks into the medical device packaging with a click. Further, the click can indicate that the medical device is secure within the medical device packaging.

In another embodiment, the medical device can be enclosed within the medical device packaging by the first protrusion, the second protrusion, a third protrusion, and a fourth protrusion, wherein the third protrusion can extend from an inner surface of the first side wall and the fourth protrusion can extend from an inner surface of the second side wall.

In still another embodiment, the third protrusion of the medical device packaging can be located between the front wall and the second protrusion in the z-direction and the fourth protrusion can be located between the front wall and the second protrusion in the z-direction.

In yet another embodiment, the second protrusion of the medical device packaging can be centrally located on the inner surface of the bottom wall.

In an additional embodiment, the eyelid speculum can be removed by rotating the finger tabs of the eyelid speculum over the first portion and the second portion of the front wall.

In one more embodiment, the eyelid speculum can be rotated by an angle of about 50° to about 100° with respect to the y-direction. Such an angle can allow for the eyelid speculum to be removed from the medical device packaging.

In another embodiment, the medical device packaging can be formed from an autoclavable material. Such a material can allow for the medical device packaging to be sterilized in an autoclave.

In still another embodiment, the medical device packaging can be formed from a sterilizable material.

In yet another embodiment, the medical device packaging can be disposable after one use.

In an additional embodiment, the medical device packaging can be formed from a thermoplastic polymer. Such a material allows for a high volume of production of medical device packaging without compromising the strength, integrity, or weight of the medical device packaging.

In one more embodiment, the medical device packaging can be formed from acrylonitrile butadiene styrene, polyethylene, polypropylene, polycarbonate, polyamide, polystyrene, polymethyl methacrylate, or a combination thereof.

In another embodiment, the medical device packaging can be formed from a biodegradable material. Such a material allows for the medical device packaging to degrade when disposed.

In another particular embodiment, the medical device packaging can be formed via injection molding, 3D printing, or thermomolding.

In still another particular embodiment, the first protrusion of the medical device packaging can have a flat bottom surface and a length shorter than the distance between the first side wall and the second side wall.

In yet another embodiment, the medical device packaging can have a width between the first side wall and the second side wall of the medical device packaging that can range from about 10 millimeters (mm) and about 50 mm.

In another embodiment, the medical device packaging can have a height in the y-direction that can range from about 5 mm and about 25 mm.

In one more particular embodiment, the distance between the outer surface of the front wall and the outer surface of the back wall can range from about 5 mm and about 25 mm.

In another particular embodiment, the width in the x-direction between the first side wall and the second side wall can range from about 10 millimeters and about 50 millimeters.

In a further embodiment, the height of the medical device packaging in the y-direction can range from about 5 millimeters and about 25 millimeters.

In an additional embodiment, the length in the z-direction between the outer surface of the front wall and the outer surface of the back wall of the medical device packaging can range from about 5 millimeters and about 25 millimeters.

Other features and aspects of the present invention are set forth in greater detail below.

BRIEF DESCRIPTION OF THE DRAWINGS

A full and enabling disclosure of the present invention to one skilled in the art, including the best mode thereof, is set forth more particularly in the remainder of the specification, including reference to the accompanying figures, in which.

Figure 1:
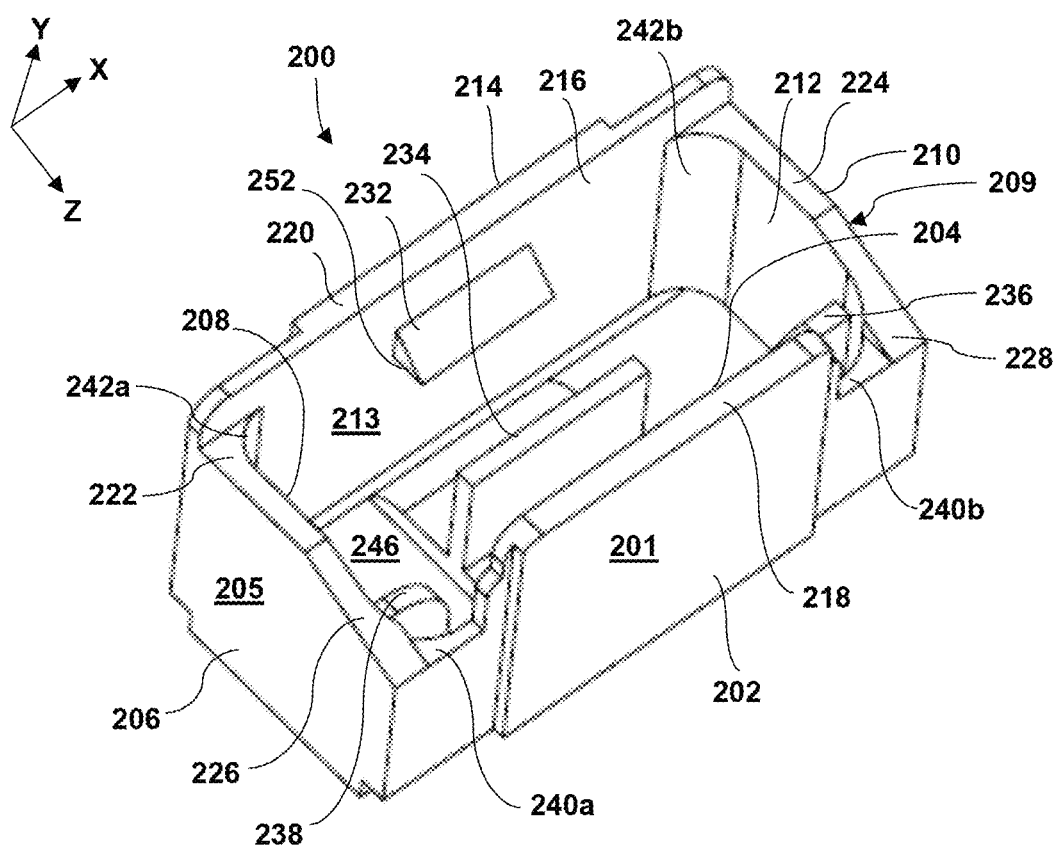
FIG. 1 is a perspective view of the packaging for a medical device according to one embodiment of the present invention.

Repeat use of reference characters in the present specification and drawings is intended to represent the same or analogous features or elements of the present invention.

DETAILED DESCRIPTION OF REPRESENTATIVE EMBODIMENTS

It is to be understood by one of ordinary skill in the art that the present discussion is a description of exemplary embodiments only and is not intended as limiting the broader aspects of the present invention.

As used herein, the terms "about," "approximately," or "generally," when used to modify a value, indicates that the value can be raised or lowered by 5% and remain within the disclosed embodiment. Further, when a plurality of ranges is provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

Generally speaking, the present invention is directed to packaging for a medical device, such as, but not limited to, an eyelid speculum. The medical device packaging includes a front wall, a back wall, a bottom wall, a first side wall, and a second side wall, wherein the front wall includes a front lip positioned between a first portion and a second portion of the front wall; wherein the front lip has a height that is greater than a height of the first portion and the second portion of the front wall; wherein a first protrusion extends from an inner surface of the front wall, wherein the front wall and the back wall extend upward from the bottom wall in a y-direction, wherein the bottom wall extends between the first side wall and the second side wall in the x-direction, and wherein the first side wall and the second side wall extend between the front wall and the back wall in the z-direction. The various features of the packaging are shown in FIGS. 1-12.

Without intending to be limited by any particular theory, the present inventors have found that the particular features of the medical device packaging of the present invention (e.g., the shapes, ratios, and dimensions of the front wall, back wall, side walls, and bottom wall as well as the placement of the various protrusions) allow for the eyelid speculum to be enclosed within the medical device packaging in a secure manner that ensures its stability during shipping while also maintaining the sterility of the eyelid speculum until it is ready to be used by a medical professional. The eyelid speculum is inserted into the medical device packaging by pressing into the medical device packaging until it locks into the medical device packaging with a click. The eyelid speculum is then removed by pushing the finger tabs of the eyelid speculum over the first portion and the second portion of the front wall.

Specifically, to load the eyelid speculum into the packaging, the eyelid speculum is pressed into the packaging with the outer side surface of the central ring of the eyelid speculum facing the front wall of the packaging. The eyelid speculum is pressed into the packaging until it locks in place with a click, where the eyelid speculum is contained within the packaging or held down by a protrusion near the top of the inner surface of the front wall of the packaging, where it is also to be understood that a protrusion may also be located near the top of the inner surface of the back wall of the packaging. Once a user is ready to remove the eyelid speculum from the packaging, the user pushes the finger tabs of the eyelid speculum toward the front wall of the packaging (see FIGS. 1, 2, and 10). This rotates the eyelid speculum by an angle of about 50° to about 100°, such as from about 60° to about 95°, such as from about 70° to about 90° to a position where the eyelid speculum can be easily released from the packaging by the user in a sterile manner by lifting the eyelid speculum by the finger tabs upward and out of the packaging.

In addition to the packaging of the present invention protecting the eyelid speculum during shipping, it also facilitates the presentation of the eyelid speculum (or any other medical device) to the user in the proper orientation for use.

For instance, the eyelid speculum is asymmetric and is grasped in one orientation for the right eye and in an opposite orientation for the left eye and also depending on if the technician grasps with their right or left hand. The eyelid speculum is placed on the eye with the central ring open either nasally or temporally depending on physician preference for the injection site. One of the problems with the eyelid speculum being packaged and shipped loose or unrestrained in a plastic bag is the level of maneuvering required to maintain the sterility of the eyelid speculum so that the finger tabs are oriented correctly for the particular technician and eye. The packaging of the present invention solves this problem in that once the eyelid speculum is rotated horizontally so that the finger tabs extend in the horizontal direction toward the front wall of the packaging, the user can turn the entire eyelid speculum as suitable to grasp the finger tabs correctly and maintain the sterility of the eyelid speculum. Additionally, the packaging with the loaded eyelid speculum can be removed from the bag and the eyelid speculum can be placed on a tray while keeping the eyelid speculum sterile until use.

In addition, the packaging can be formed from autoclavable and/or sterilizable materials that can also be disposable. For instance, the packaging can be formed from a thermoplastic polymer. Although any suitable thermoplastic polymer can be used to form the packaging of the present invention, in one particular embodiment, the packaging can be formed from acrylonitrile butadiene styrene, polyethylene, polypropylene, polycarbonate, polyamide, polystyrene, polymethyl methacrylate, or a combination thereof. In other embodiments, the packaging can be formed from any suitable biodegradable material. Moreover, it is to be understood that the packaging can be formed via injection molding, 3D printing, thermomolding, or any other suitable method.

Various embodiments of the present invention will now be described in more detail.

Figure 2:
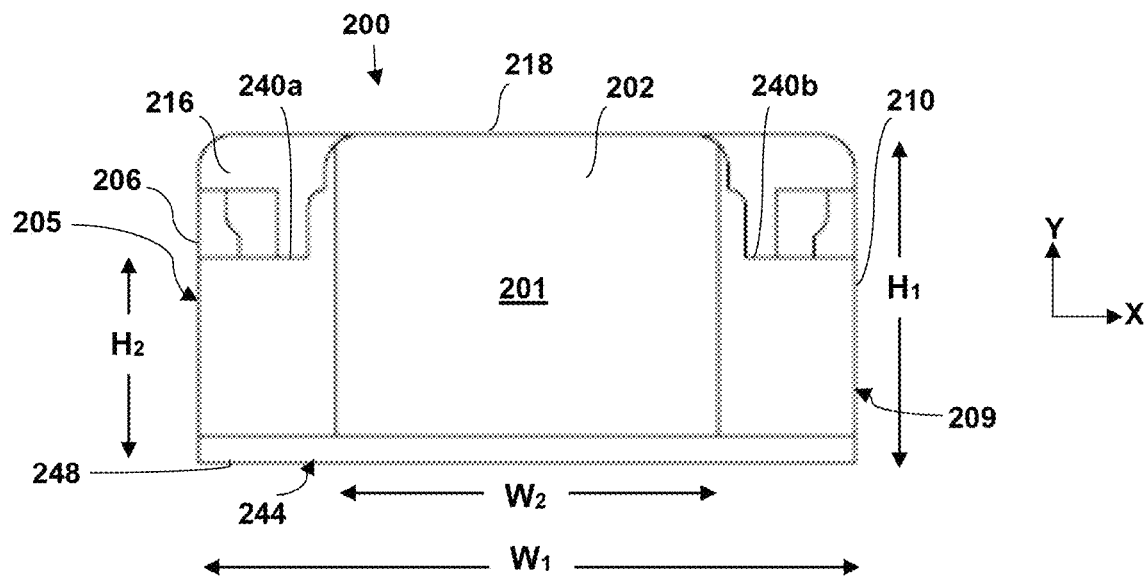
FIG. 2 is a front view of the packaging of FIG. 1.
Figure 3:
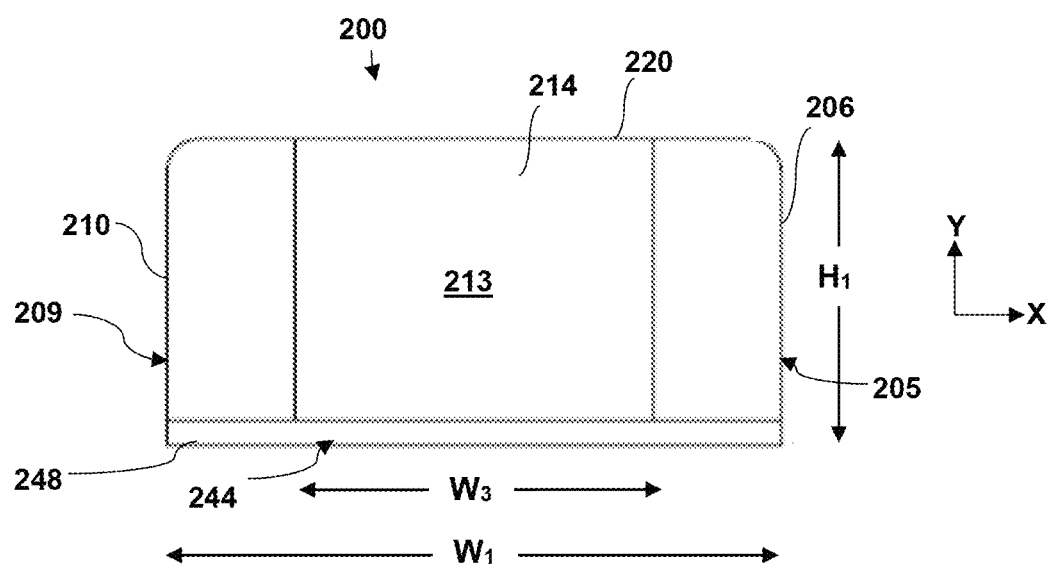
FIG. 3 is a back view of the packaging of FIG. 1.
Figure 4:
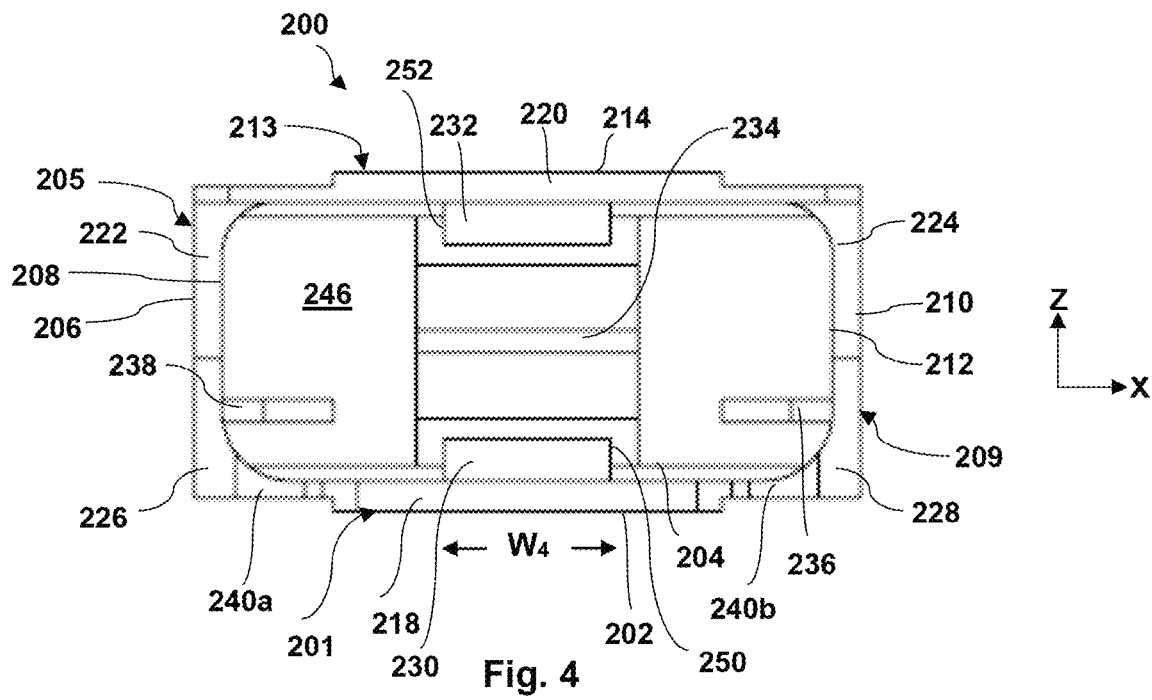
FIG. 4 is a top view of the packaging of FIG. 1.
Figure 5:
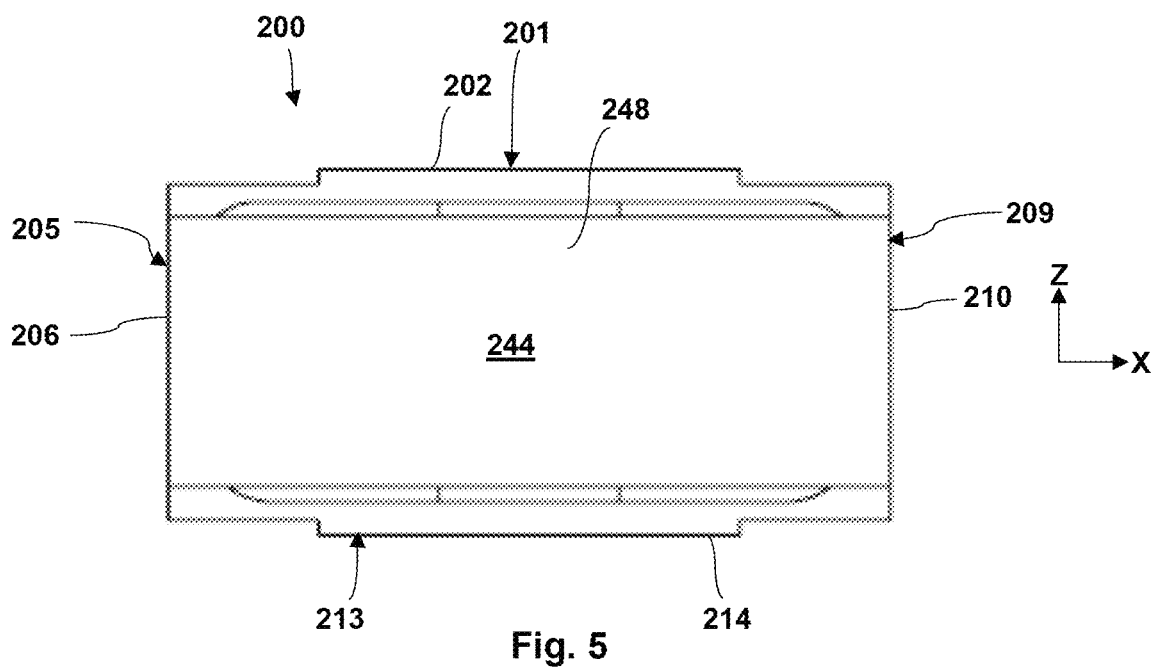
FIG. 5 is a bottom view of the packaging of FIG. 1.
Figure 6:
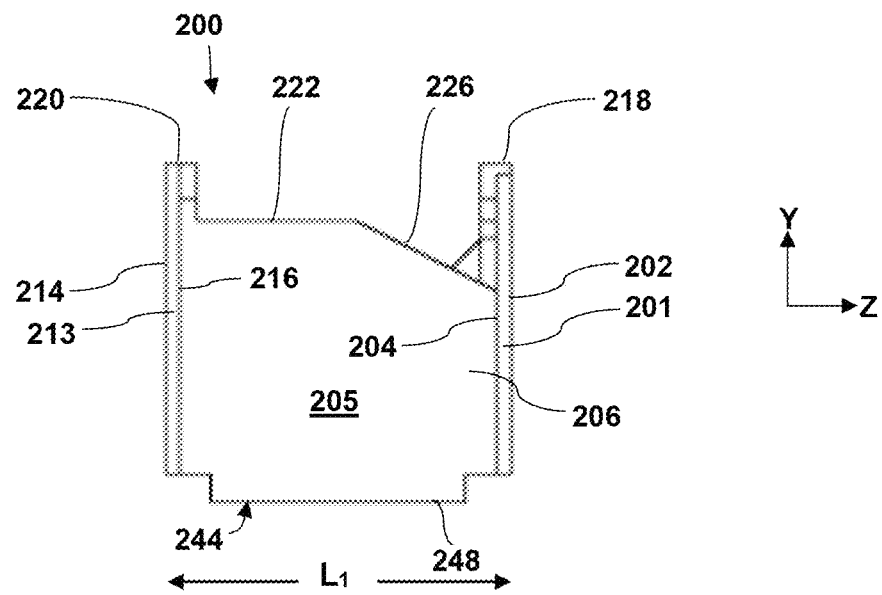
FIG. 6 is a left side view of the packaging of FIG. 1.
Figure 7:
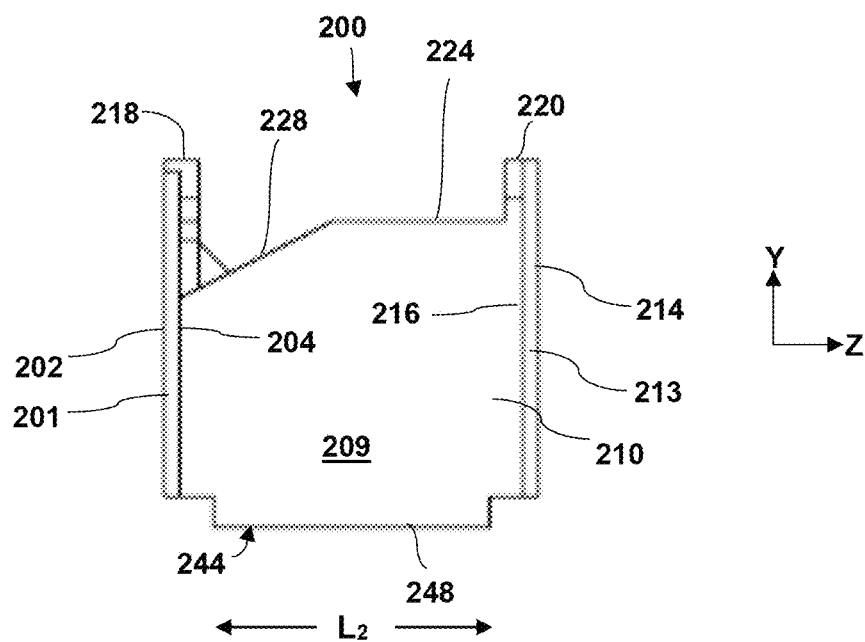
FIG. 7 is a right side view of the packaging of FIG. 1.
Figure 12:
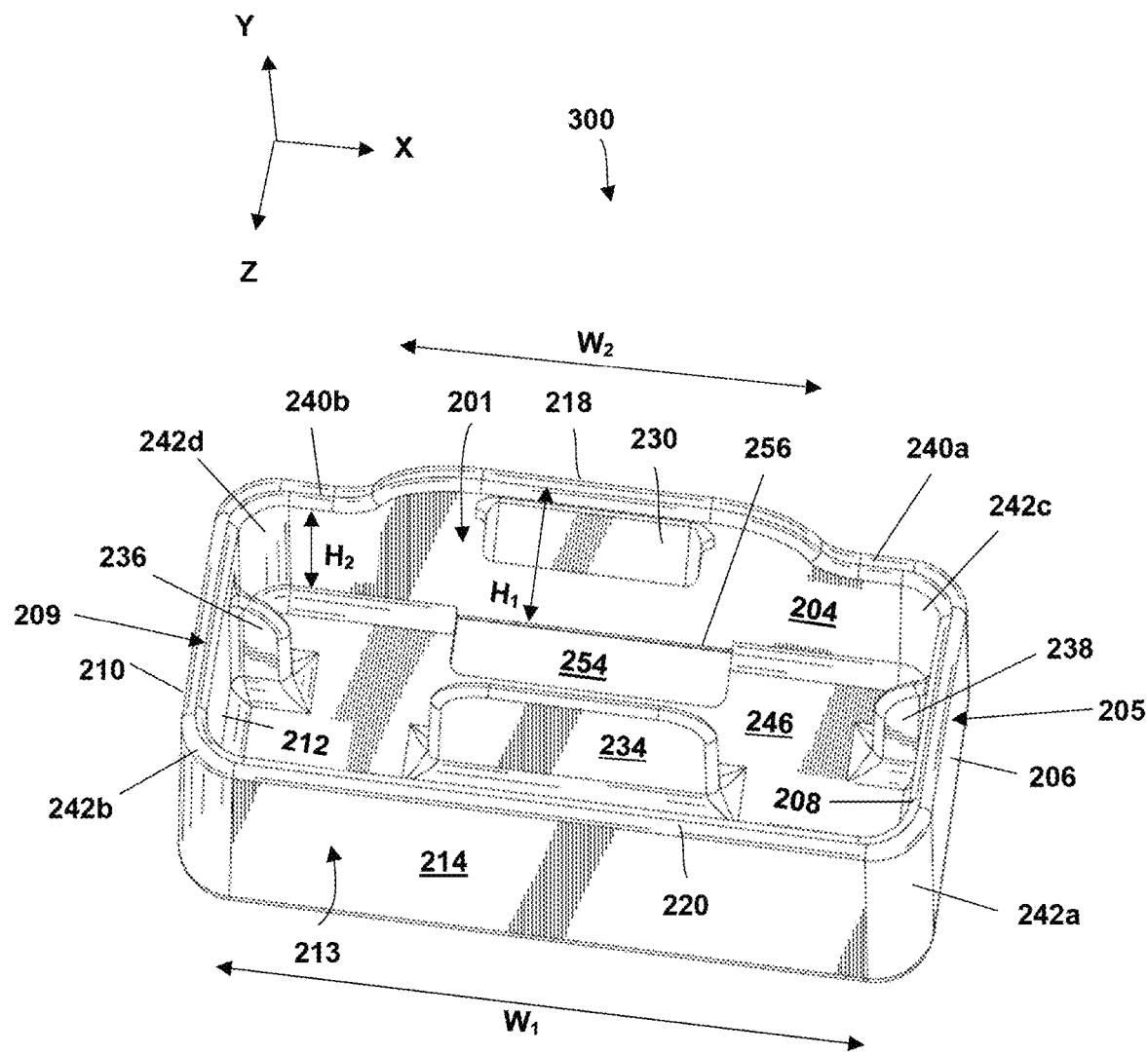
FIG. 12 is a perspective view of the packaging for a medical device according to another embodiment of the present invention.

Referring now to FIGS. 1-7 and 12, the particular components of various embodiments of the medical device packaging 200 and 300 of the present invention are shown. Specifically, FIG. 1 is a perspective view of the packaging for a medical device 200 of the present invention. FIG. 2 is a front view of the packaging 200 of the present invention. FIG. 3 is a back view of the packaging 200 of the present invention. FIG. 4 is a top view of the packaging 200 of the present invention. FIG. 5 is a bottom view of the packaging 200 of the present invention. FIG. 6 is a left side view of the packaging 200 of the present invention. FIG. 7 is a right side view of the packaging 200 of the present invention. FIG. 12 is a perspective view of the packaging for a medical device 300 according to another embodiment of the present invention.

The medical device packaging 200 includes a front wall 201, a back wall 213, a bottom wall 244, a first side wall 205, and a second side wall 209. The front wall 201 and the back wall 213 extend upwardly from the bottom wall 244 in a y-direction. The front wall 201 includes an outer surface 202 and an inner surface 204. The front wall 201 includes a front lip 218 which extends out of the front wall 201 in the z-direction. The front lip 218 of the front wall 201 is centered on the front wall 201 in the x-direction but has a shorter width $W_2$ than the width $W_1$ of the front wall 201 in the x-direction. The front lip 218 also has a height $H_1$ which is greater than a height $H_2$ of the first portion 240*a* of the front wall 201 and the second portion 240*b* of the front wall 201 between which the front lip 218 is positioned in the y-direction. Because of these features of the front lip 218, the first portion 240*a* and the second portion 240*b* of the front wall 201 are necessarily created that have a height $H_2$ that is lesser than the height of the front lip 218. The first portion 240*a* connects the front lip 218 to the first side wall 205, while the second portion 240*b* connects the front lip 218 to the second side wall 209.

The back wall 213 includes an outer surface 214 and an inner surface 216. The back wall 213 also include a back lip 220 which protrudes from the back wall 213 in the z-direction. The back lip 220 is centered on the back wall 213 in the x-direction but has a shorter width $W_3$ than width $W_1$ of the back wall 213 in the x-direction. The back lip 220 can have a height which is equal to or greater than height $H_1$ of the back wall 213 in the y-direction as shown.

The bottom wall 244 extends between the first side wall 205 and the second side wall 209 in the x-direction. The bottom wall 244 extends below the front wall 201, the back wall 213, first side wall 205, the second side wall 209 in the y-direction. The extension of the bottom wall 244 in the y-direction can create a stepped portion with the bottom wall 244 being the lower stepped portion and the front wall 201 and back wall 213 being the higher stepped portion. The bottom wall 244 has an inner surface 246 and an outer surface 248.

The first side wall 205 and the second side wall 209 extend between the front wall 201 and the back wall 213 in the z-direction. The first side wall 205 and second side wall 209 are connected to the back wall 213 with a curved wall connector 242*a* and the curved wall connector 242*b*, respectively, for each side. The first side wall 205 is connected to the back wall 213 with the curved wall connector 242*a*. The second side wall 209 is connected to the back wall 213 with the curved wall connector 242*b*. The curved wall connectors 242*a* and 242*b* are curved on an axis rotating in the z-x plane with their respective curved portion facing the interior of the medical device packaging 200. The first side wall 205 has an outer surface 206, an inner surface 208, an upper surface 222. The second side wall has an outer surface 210, an inner surface 212, and an upper surface 224. The first side wall 205 also defines a sloped upper first side wall portion 226 which connects to the first portion 240a of the front wall 201. Further, the sloped upper first side wall portion 226 has a height which decreases in the z-direction toward the first portion 240a of the front wall 201. The second side wall 209 also defines a sloped upper second side wall portion 228 which connects to the second portion 240b of the front wall 201. The sloped upper second side wall portion 228 also has a height which decreases in the z-direction toward the second portion 240b of the front wall 201.

A first protrusion 230 of the medical device packaging 200 extends from an inner surface 204 of the front wall 201 and a second protrusion can 234 extend from an inner surface 246 of the bottom wall 244. The first protrusion 230 of the medical device packaging 200 has a flat bottom surface 250 facing the inner surface 246 of the bottom wall 244 and a width $W_4$ that is shorter than the width $W_1$ between the first side wall 205 and the second side wall 209 in the x-direction. The first protrusion 230 extends from an inner surface 204 of the front wall 201 at a height in the y-direction which allows for the secure placement of a medical device 100. The second protrusion 234 of the medical device packaging 200 can be centrally located on the inner surface 246 of the bottom wall 244 in the x-direction and the z-direction. If present, the second protrusion 234 can extend upwardly from the inner surface 246 of the bottom wall 244 to a height in the y-direction which allows for the secure placement of a medical device. A third protrusion 236 of the medical device packaging 200 extends from an inner surface 212 of the second side wall 209 in the x-direction and is located between the front wall 201 and the second protrusion 234 in the z-direction to allow for the secure placement of a medical device. A fourth protrusion 238 of the medical device packaging 200 extends from an inner surface 208 of the first side wall 205 in the x-direction and is located between the front wall 201 and the second protrusion 234 in the z-direction to allow for the secure placement of a medical device. Although not required, the medical device packaging 200 can also include a fifth protrusion 232 that can extend from an inner surface 216 of the back wall 213 as shown in FIGS. 1 and 4. The fifth protrusion 232 of the medical device packaging 200 can have a flat bottom surface 250 facing the inner surface 246 of the bottom wall 244 and a width $W_4$ that is shorter than the width $W_1$ between the first side wall 205 and the second side wall 209 in the x-direction. The fifth protrusion 232 can extend from an inner surface 216 of the back wall 213 at a height in the y-direction which allows for the secure placement of a medical device 100.

On the other hand, FIG. 12 illustrates an embodiment of the medical device packaging 300 that does not require the fifth protrusion 232 as shown in FIGS. 1 and 4. The medical device packaging 300 includes a front wall 201, a back wall 213, a bottom wall 244, a first side wall 205, and a second side wall 209. The front wall 201 and the back wall 213 extend upwardly from the bottom wall 244 in a y-direction. The front wall 201 includes an outer surface 202 (not shown, but refer to FIG. 2) and an inner surface 204. The front wall 201 also includes a front lip 218 which extends out of the front wall 201 in the z-direction. The front lip 218 of the front wall 201 is centered on the front wall 201 in the x-direction but has a shorter width $W_2$ than the width $W_1$ of the front wall 201 in the x-direction. The front lip 218 also has a maximum height $H_1$ which is greater than a height $H_2$ of the first portion 240a of the front wall 201 and the second portion 240b of the front wall 201 between which the front lip 218 is positioned in the y-direction. Because of these features of the front lip 218, the first portion 240a and the second portion 240b of the front wall 201 are necessarily created that have a height $H_2$ that is less than the height of the front lip 218. The first portion 240a connects the front lip 218 to a curved wall connector 242c, while the second portion 240b connects the front lip 218 to a curved call connector 242d.

The back wall 213 includes an outer surface 214 and an inner surface 216 (not shown but refer to FIG. 1). The back wall 213 also include a back lip 220 which protrudes from the back wall 213 in the z-direction. The first side wall 205 and the second side wall 209 extend between the front wall 201 and the back wall 213 in the z-direction. The first side wall 205 and second side wall 209 are connected to the back wall 213 with a curved wall connector 242a and a curved wall connector 242b, respectively, for each side. The first side wall 205 and second side wall 209 are connected to the front wall 201 with the curved wall connector 242c and the curved wall connector 242d, respectively, for each side. The curved wall connectors 242a, 242b, 242c, and 242d are curved on an axis rotating in the z-x plane with their respective curved portion facing the interior of the medical device packaging 300.

As shown, a first protrusion 230 of the medical device packaging 300 extends from an inner surface 204 of the front wall 201 and a second protrusion 234 extends from an inner surface 246 of the bottom wall 244. The first protrusion 230 extends from an inner surface 204 of the front wall 201 at a height in the y-direction which allows for the secure placement of a medical device 100. The second protrusion 234 of the medical device packaging 300 is centrally located on the inner surface 246 of the bottom wall 244 in the x-direction and the z-direction. The second protrusion 234 extends upwardly from the inner surface 246 of the bottom wall 244 to a height in the y-direction which allows for the secure placement of a medical device. A third protrusion 236 of the medical device packaging 300 extends from an inner surface 212 of the second side wall 209 in the x-direction and is located between the front wall 201 and the second protrusion 234 in the z-direction to allow for the secure placement of a medical device. A fourth protrusion 238 of the medical device packaging 300 extends from an inner surface 208 of the first side wall 205 in the x-direction and is located between the front wall 201 and the second protrusion 234 in the z-direction to allow for the secure placement of a medical device 100.

Additionally, the medical device packaging 300 of FIG. 12 can also include an opening 254 present on the bottom wall 246 adjacent the front wall 201. The opening 254 is positioned under the first protrusion 230 and between the second protrusion 234 and a lower edge 256 of the inner surface 204 as shown. The opening can allow for a less expensive mold and can also provide for a better molding process during the manufacture of the medical device packaging 300.

Regardless of the particular design of the medical device packaging 200 or 300 and referring to FIG. 2, the medical device packaging 200 can have a width $W_1$ in the x-direction between the first side wall 205 and the second side wall 209 ranging from about 10 mm to about 50 mm, such as from about 15 mm to about 45 mm, such as from about 20 mm to about 40 mm. In one particular embodiment, the width $W_1$ can be about 30 mm. The medical device packaging 200 further includes a width $W_2$ in the x-direction for the front lip 218 ranging from about 4 mm to about 30 mm, such as from about 8 mm to about 26 mm, such as from about 12 mm to about 22 mm. In one embodiment, the width $W_2$ can be about 20 mm. The medical device packaging 200 also includes a height $H_1$ in the y-direction as measured from the bottom wall 244 ranging from about 5 mm to about 25 mm, such as from about 10 mm to about 20 mm, such as from about 12.5 mm to about 17.5 mm. In one particular embodiment, the height $H_2$ can be about 15 mm. The medical device packaging 200 additionally includes a height $H_2$ in the y-direction for the lower front surface of packaging 240 that can range from about 3 mm to about 22 mm, such as from about 4 mm to about 18 mm, such as from about 6 mm to about 12 mm. In one embodiment, the height $H_2$ can be about 8 mm.

Further, as shown in FIG. 3, the medical device packaging 200 includes a width $W_3$ in the x-direction for the back lip 220 that can range from about 4 mm to about 30 mm, such as from about 8 mm to about 26 mm, such as from about 12 mm to about 22 mm. In one embodiment, the width $W_3$ can be about 20 mm.

Furthermore, as shown in FIG. 4, the medical device packaging 200 includes a width $W_4$ as in the x-direction for the first protrusion 230 and the fifth protrusion 232 that can range from about 2 mm to about 15 mm, such as from about 4 mm to about 11 mm, such as from about 6 mm to about 9 mm. In one embodiment, the width $W_4$ can be about 8 mm.

In addition, as shown in FIG. 6 and FIG. 7, the distance between the outer surface 202 of the front wall 201 and the outer surface 241 of the back wall 213 form the length of the medical device $L_1$ in the z-direction. The length $L_2$ of the bottom wall 244 defines a base for the medical device packaging in the z-direction. The medical device packaging 200 can have a length $L_1$ between the outer surface 202 of the front wall 201 and the outer surface 214 of the back wall 213 ranging from about 5 mm to about 25 mm, such as from about 10 mm to about 20 mm, such as about 12.5 mm to about 17.5 mm. In one particular embodiment, the length $L_1$ can be about 15 mm. Meanwhile, the bottom wall 244 of the medical device packaging 200 can have a length $L_2$-ranging from about 2.5 mm to about 20 mm, such as from about 5 mm to about 15 mm, such as from about 7.5 mm to about 12.5 mm. In one particular embodiment, the length $L_2$ can be about 11 mm. Moreover, the ratio of $L_1/L_2$ can range from about 1.0 to about 1.5, such as from about 1.30 to about 1.40.

Without intending to be limited by any particular theory, the present inventors have found that utilizing the particular length, height, and width dimensions and ratios described allows for the best placement of a medical device or the eye speculum 100 to ensure its stability during shipment and its sterility until use.

Figure 8:
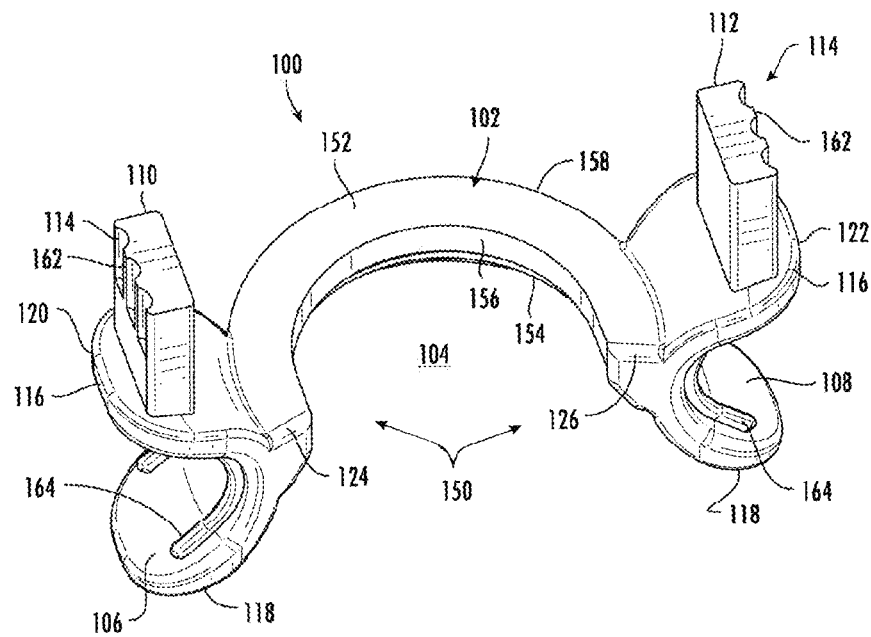
FIG. 8 is a perspective view of a medical device (e.g., an eyelid speculum) that can be disposed within the packaging of FIG. 1 as contemplated by the present invention.

Turning now to FIG. 8, one example of a medical device, in this case an eyelid speculum 100, that can be used in conjunction with the packaging of the present application is shown in more detail for understanding of how the device is loaded into and unloaded or removed from the packaging of the present invention. Specifically, FIG. 8 is a perspective view of the eyelid speculum 100. The eyelid speculum 100 includes a central ring 102 extending in a horizontal or x-direction and having an upper surface 152, a lower surface 154, an inner side surface 156, an outer side surface 158, a first end 124, and a second end 126. The first end 124 and the second end 126 are separated by a gap 150, and the central ring defines an opening 104, where such opening 104 allows a health care provider to have an unobstructed view of the desired portions of a patient's eye for then conducting any number of diagnostic and/or treatment procedures. The eyelid speculum 100 also includes a first eyelid margin holder 106 and a second eyelid margin holder 108 that both extend outwardly from the outer side surface 158 of the central ring at the first end 124 and the second end 126, respectively, where each eyelid margin holder 106, 108 has an upper portion 116 and a lower portion 118 that are separated by a central portion 160. Further, the central portion 160 of the first eyelid margin holder 106 and the central portion 160 of the second eyelid margin holder 108 each contact the outer side surface 158 of the central ring 102. As described above, the first lid margin holder 106 and the second lid margin holder 108 are spaced apart from each other by an angle θ that is defined as the angle between the first end 124 and the second end 126 of the central ring 102 of the eyelid speculum 100, where the θ ranges from about 120° to about 185°, such as from about 125° to about 175°, such as from about 135° about 165°. Additionally, the upper portions 116 and the lower portions 118 of the first lid margin holder 106 and the second lid margin holder 108 can be curved (e.g., c-shaped or semicircular) to form a scoop-like shape to easily hold a patient's eyelids and eyelashes when the eyelid speculum 100 is inserted into an eye of a patient.

In addition, the eyelid speculum 100 includes a first finger tab 110 and a second finger tab 112 that extend upwardly in the vertical or y-direction, for instance, next to or adjacent the outer edge 120 and the outer edge 122 of the upper portions 116 of the first eyelid margin holder 106 and the second eyelid margin holder 108. As shown in FIG. 8, the first finger tab 110 and the second finger tab 112 can either be straight, or, in some embodiments (not shown), the first finger tab 110 and the second finger tab 112 can be curved (e.g., semicircular or c-shaped), where the curved-shape can correspond with the curved-shape of the outer edge 120 and the outer edge 122 of the upper portions 116 of the first eyelid margin holder 106 and the second eyelid margin holder 108. Further, the outer surface 114 of the finger tabs 110 and 112 can be textured to enable the health care provider to easily grasp the finger tabs 110 and 112 during insertion and rotation of the eyelid speculum 100. For example, the outer surface 114 can include a plurality of ridges 162 or any other suitable texturing means.

In addition, as shown in FIG. 8, the central portion 120 as well as the upper portion 116 and lower portion 118 of the first eyelid margin holder 106 and the second eyelid margin holder 108 can include one or more ridges 164. The ridges 164 help to maintain the eyelid speculum 100 in the proper position when being used on a patient by counteracting any movement of the eyelid speculum 100 that might be caused by a patient squeezing or trying to close his or her eyelids, which could lead to counter rotation and misalignment of the eyelid speculum 100. Without intending to be limited by any particular theory, the present inventors have found that the ridges 164 on the inner surfaces of the first eyelid margin holder 106 and the second eyelid margin holder 108 can prevent movement of the eyelid speculum 100 when aligned perpendicular to the direction of the eyelid movement.

Figure 9:
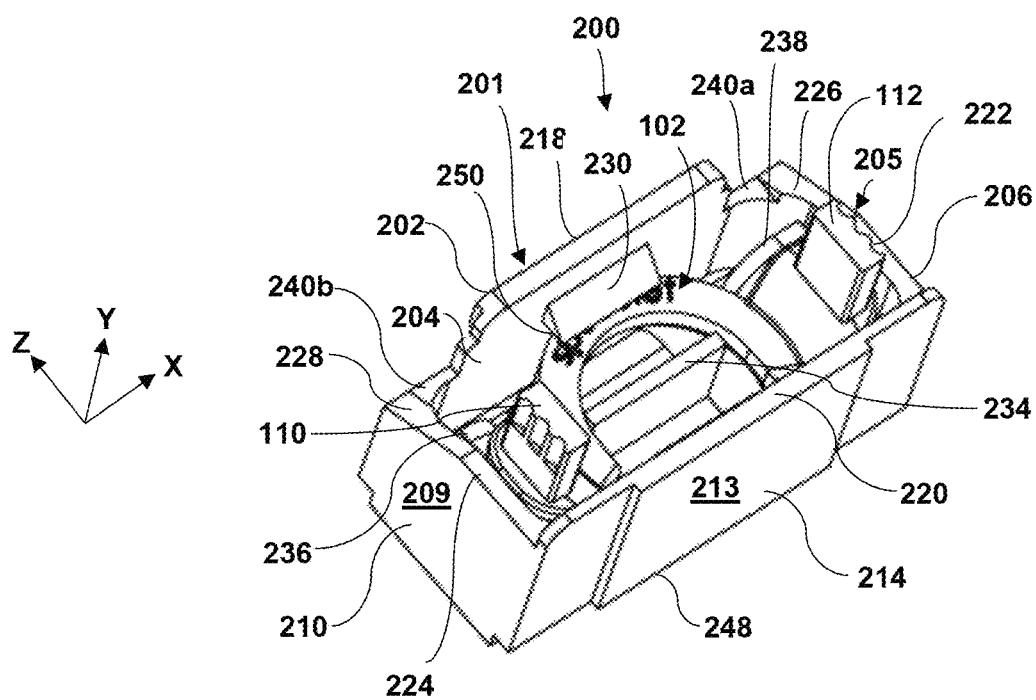
FIG. 9 is a perspective view of the eyelid speculum of FIG. 8 when it is loaded into the packaging of FIG. 1.
Figure 10:
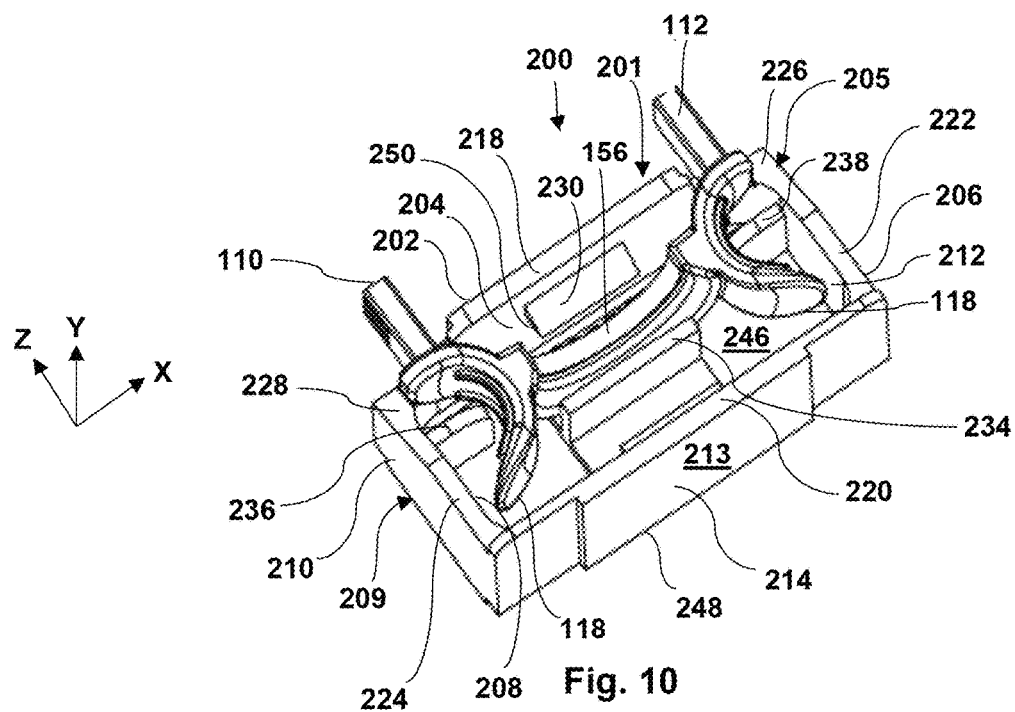
FIG. 10 is a perspective view of the eyelid speculum of FIG. 8 as it is being removed from the packaging of FIG. 1.
Figure 11:
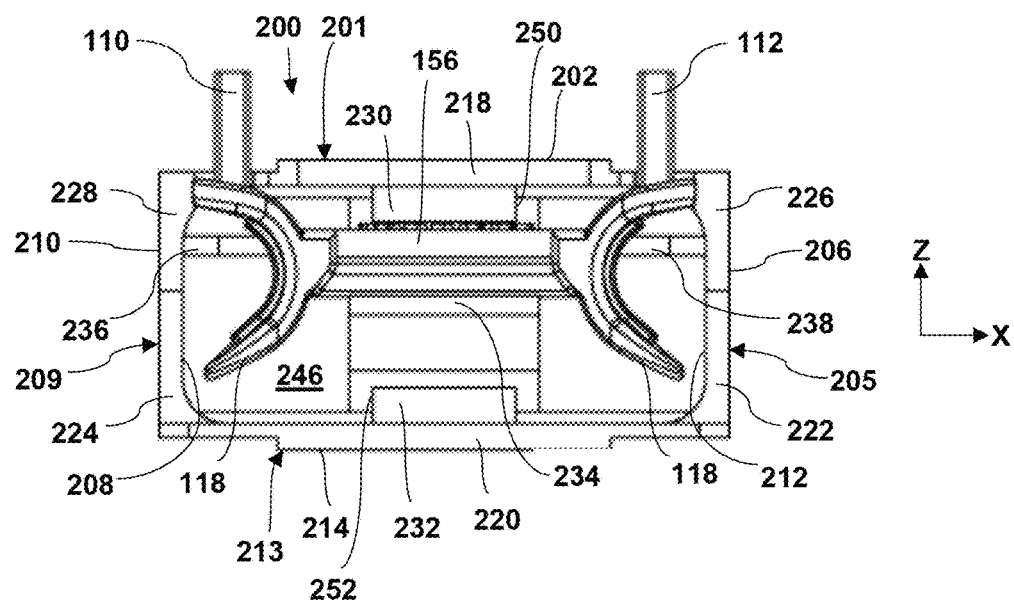
FIG. 11 is a top view of the eyelid speculum of FIG. 8 as it is being removed from the packaging of FIG. 1.

Additionally, as shown in FIG. 9-11, the eyelid speculum 100 can be inserted into the medical device packaging 200. To load the eyelid speculum 100 into the medical device packaging 200, the eyelid speculum 100 is pressed into the medical device packaging 200 with the outer side surface 158 of the central ring 102 of the eyelid speculum 100 facing the front wall 201 of the medical device packaging 200. The eyelid speculum 100 is pressed into the medical device packaging 200 until it locks in place with a click, where the eyelid speculum 100 is contained within the medical device packaging 200 or held down by the first protrusion 230 and fifth protrusion 232 (if present) near the top of the inner surface 204 of the front wall 201 and the inner surface 216 of the back wall 213 of the packaging 200. Once a user is ready to remove the eyelid speculum 100 from the packaging 200, the user pushes the finger tab 110 and finger tab 112 of the eyelid speculum 100 toward the front wall 201 of the packaging 200. This rotates the eyelid speculum 100 by an angle of about 50° to about 100°, such as from about 60° to about 95°, such as from about 70° to about 90° to a position where the eyelid speculum 100 can be easily released from the packaging 200 by the user in a sterile manner by lifting the eyelid speculum 100 by the finger tab 110 and finger tab 112 upward and out of the packaging 200.

Referring now to FIG. 9, the eyelid speculum 100 is held in place in the packaging 200 (or 300) by the first protrusion 230, the first protrusion 230 extending over the central ring 102 in the z-direction and applying downward force on the central ring 102 in the y-direction. The eyelid speculum 100 may be further held in place by the fifth protrusion 232, the fifth protrusion 232 extending over the first end of the central ring 124 and the second end of the central ring 126 in the z-direction and applying downward force on first end of the central ring 124 and the second end of the central ring 126 in the y-direction. The eyelid speculum 100 is still further held in place by the second protrusion 234 extending through the gap between the edges of the central ring 150 in the y-direction and applying horizontal force on the edges of the central ring 102 in the x-direction. The eyelid speculum 100 is even further held in place by the third protrusion 236 and the fourth protrusion 238 extending along the first lid margin holder 106 and the second lid margin holder 108 in the x-direction and applying lateral force on the first lid margin holder 106 and the second lid margin holder 108 in the z-direction.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only and is not intended to limit the invention so further described in such appended claims.

What is claimed is:

1. A medical device packaging for housing a medical device, the medical device packaging comprising:
   a front wall, a back wall, a bottom wall, a first side wall, and a second side wall, wherein the front wall includes a front lip positioned between a first portion and a second portion of the front wall; wherein the front lip has a height that is greater than a height of the first portion and the second portion of the front wall; wherein a first protrusion extends directly from an inner surface of the front wall in a fixed position and has a flat bottom surface that faces and is spaced apart from an inner surface of the bottom wall in a y-direction, wherein the front wall and the back wall extend upward from the bottom wall in the y-direction, wherein the bottom wall extends between the first side wall and the second side wall in an x-direction, and wherein the first side wall and the second side wall extend between the front wall and the back wall in a z-direction.

2. The medical device packaging of claim 1, wherein an opening is present on the bottom wall adjacent the front wall and wherein a second protrusion extends from an inner surface of the bottom wall.

3. The medical device packaging of claim 2, wherein the medical device is an eyelid speculum comprising:
   a central ring having an upper surface, a lower surface, an inner side surface, an outer side surface, a first end, and a second end, wherein the first end and the second end are separated by a gap, and wherein the central ring defines an opening;
   a first eyelid margin holder extending outwardly from the outer side surface of the central ring at the first end and having an upper portion and a lower portion;
   a second eyelid margin holder extending outwardly from the outer side surface of the central ring at the second end and having an upper portion and a lower portion;
   a first finger tab extending upwardly from the upper portion of the first eyelid margin holder; and
   a second finger tab extending upwardly from the upper portion of the second eyelid margin holder.

4. The medical device packaging of claim 3, wherein the eyelid speculum is pressed into the medical device packaging with the outer surface of the eyelid speculum facing the front wall of the medical device packaging.

5. The medical device packaging of claim 3, wherein the eyelid speculum is pressed into the medical device packaging until it locks into the medical device packaging with a click.

6. The medical device packaging of claim 2, wherein the medical device is enclosed within the medical device packaging by the first protrusion, the second protrusion, a third protrusion, and a fourth protrusion, wherein the third protrusion extends from an inner surface of the first side wall and the fourth protrusion extends from an inner surface of the second side wall.

7. The medical device packaging of claim 6, wherein the third protrusion is located between the front wall and the second protrusion in the z-direction and the fourth protrusion is located between the front wall and the second protrusion in the z-direction.

8. The medical device packaging of claim 6, wherein the second protrusion is centrally located on the inner surface of the bottom wall.

9. The medical device packaging of claim 3, wherein the eyelid speculum is removed by rotating the finger tabs of the eyelid speculum over the first portion and the second portion of the front wall.

10. The medical device packaging of claim 9, wherein the eyelid speculum can be rotated by an angle of about 50° to about 100° with respect to the y-direction.

11. The medical device packaging of claim 1, wherein the medical device packaging is formed from an autoclavable material.

12. The medical device packaging of claim 1, wherein the medical device packaging is formed from a sterilizable material.

13. The medical device packaging of claim 1, wherein the medical device packaging is disposable after one use.

14. The medical device packaging of claim 1, wherein the medical device packaging is formed from a thermoplastic polymer.

15. The medical device packaging of claim 12, wherein the medical device packaging is formed from acrylonitrile butadiene styrene, polyethylene, polypropylene, polycarbonate, polyamide, polystyrene, polymethyl methacrylate, or a combination thereof.

16. The medical device packaging of claim 1, wherein the medical device packaging is formed from biodegradable material.

17. The medical device packaging of claim 1, wherein the medical device packaging is formed via injection molding, 3D printing, or thermomolding.

18. The medical device packaging of claim 1, wherein the first protrusion has a length shorter than the distance between the first side wall and the second side wall.

19. The medical device packaging of claim 1, wherein a width in the x-direction between the first side wall and the second side wall ranges from about 10 millimeters and about 50 millimeters.

20. The medical device packaging of claim 1, wherein the medical device packaging has a height in the y-direction ranging from about 5 millimeters and about 25 millimeters.

21. The medical device packaging of claim 1, wherein a length in the z-direction between the outer surface of the front wall and the outer surface of the back wall ranges from about 5 millimeters and about 25 millimeters.

* * * * *